United States Patent [19]
Pugh

[11] Patent Number: 5,671,734
[45] Date of Patent: Sep. 30, 1997

[54] AUTOMATIC MEDICAL SIGN MONITOR

[75] Inventor: Jamie K. Pugh, San Diego, Calif.

[73] Assignee: The United States of America as represented by the Secretary of the Navy, Washington, D.C.

[21] Appl. No.: 552,818

[22] Filed: Nov. 3, 1995

[51] Int. Cl.⁶ ........................................ A61B 5/00
[52] U.S. Cl. .................. 128/630; 128/630; 128/671; 128/637; 128/668; 128/687; 128/670; 128/672
[58] Field of Search ................... 128/671, 630, 128/637, 668, 687, 670, 672, 691, 695 R, 716, 725; 364/413.03, 413.02, 415, 416

[56] References Cited

U.S. PATENT DOCUMENTS

| | | |
|---|---|---|
| 4,197,854 | 4/1980 | Kasa . |
| 4,396,020 | 8/1983 | Wolff et al. . |
| 4,461,301 | 7/1984 | Ochs . |
| 4,506,678 | 3/1985 | Russell et al. . |
| 4,665,485 | 5/1987 | Lundy et al. . |
| 4,779,199 | 10/1988 | Yoneda et al. . |
| 4,803,625 | 2/1989 | Fu et al. . |
| 4,852,570 | 8/1989 | Levine . |
| 4,872,122 | 10/1989 | Altschuler et al. . |
| 4,889,132 | 12/1989 | Hutcheson et al. . |
| 4,899,758 | 2/1990 | Finkelstein et al. . |
| 5,036,852 | 8/1991 | Leishman ................... 128/630 |
| 5,121,467 | 6/1992 | Skeirik ....................... 395/11 |
| 5,199,439 | 4/1993 | Zimmerman et al. . |
| 5,226,416 | 7/1993 | Berthune et al. ........... 128/630 |
| 5,239,456 | 8/1993 | Badavas et al. . |
| 5,253,531 | 10/1993 | Walker et al. .............. 73/650 |
| 5,309,919 | 5/1994 | Snell et al. . |
| 5,331,549 | 7/1994 | Crawford, Jr. . |
| 5,365,922 | 11/1994 | Raemer . |
| 5,464,012 | 11/1995 | Falcone ...................... 128/630 |

Primary Examiner—Jennifer Bahr
Assistant Examiner—Stephen Huang
Attorney, Agent, or Firm—Harvey FEndelman; Michael A. Kagan; Eric James Whitesell

[57] ABSTRACT

An automatic medical monitor of the present invention comprises medical sign sensors for collecting a time-ordered set of values representative of medical signs such as pulse, respiration, and blood pressure. The medical sign sensors are coupled to a medical sign data processor that forms statistics from the medical sign data and forms a modified Fast Initial Response (FIR) Shewhart cumulative sum and a variance cumulative sum to detect changes in health state. When a change in health state is detected, the medical sign data processor displays the statistics on a display and logs them on a printer.

14 Claims, 4 Drawing Sheets

AUTOMATIC MEDICAL SIGN MONITOR

BACKGROUND OF THE INVENTION

The present invention relates to medical sign monitors. More specifically, but without limitation thereto, the present invention relates to an automatic medical sign monitor for detecting and reporting changes in health state of medical patients.

A disease may be described in terms of a set of signs and symptoms. The sentinel event, a shift in a sign or symptom, is a shift toward or away from a state of "wellness". Medical signs comprise the set of measurable variables such as systolic blood pressure, diastolic blood pressure, temperature, weight, etc. Medical symptoms are a set of indicators such as headache, dizziness, blurred vision, etc.

If an individual is currently in good health, a base line may be obtained for that individual's medical signs. Once a base line has been established, statistical algorithms may be applied to the medical sign data to alert medical personnel to changes that may indicate the onset of disease, effects of medication, patient treatment compliance, and disease reaction episodes. Changes in medical signs that may be important are shifts in mean, trends up or down in the mean, transients, and changes in the variance. A medical sign change may occur gradually over time or may shift within a short time frame. Although a shift in medical signs represents a change in health status, the resultant value may still be within a normal range. Information about the size, direction, and time of the change is important in determining health status, cause of disease and reaction to treatment. Curve fitting techniques may also be used to forecast future values of medical signs from past values.

A need therefore exists in the health care industry not only to monitor medical signs, but to detect and report changes in the medical signs that signal changes in the health status of medical patients.

SUMMARY OF THE INVENTION

The automatic medical monitor of the present invention is directed to addressing the needs described above, and may provide further related advantages. The embodiment presented in the following description of an automatic medical monitor does not preclude other embodiments and advantages of the present invention that may exist or become obvious to those skilled in the art.

The automatic medical monitor comprises medical sign sensors for collecting a time-ordered set of values representative of medical signs such as pulse, respiration, and blood pressure. The medical sign sensors are coupled to a medical sign data processor that forms statistics from the medical sign data and forms a modified Fast Initial Response (FIR) Shewhart cumulative sum and a variance cumulative sum from the statistics to detect changes in health state. When a change in health state is detected, the medical sign data processor displays the statistics on a display and logs them on a printer.

An advantage of the automatic medical sign monitor is that changes in health status are automatically detected and reported, reducing the time demands on medical staff and the possibility of failing to notice a change in health status that may require immediate attention.

Another advantage is that future values of medical signs may be predicted from past values using multivariate regression techniques.

Yet another advantage is that patient compliance with prescribed medications may be monitored and verified.

The features and advantages summarized above in addition to other aspects of the present invention will become more apparent from the description, presented in conjunction with the following drawings.

DESCRIPTION OF THE INVENTION

The following description is presented solely for the purpose of disclosing how the present invention may be made and used. The scope of the invention is defined by the claims.

Figure 1:
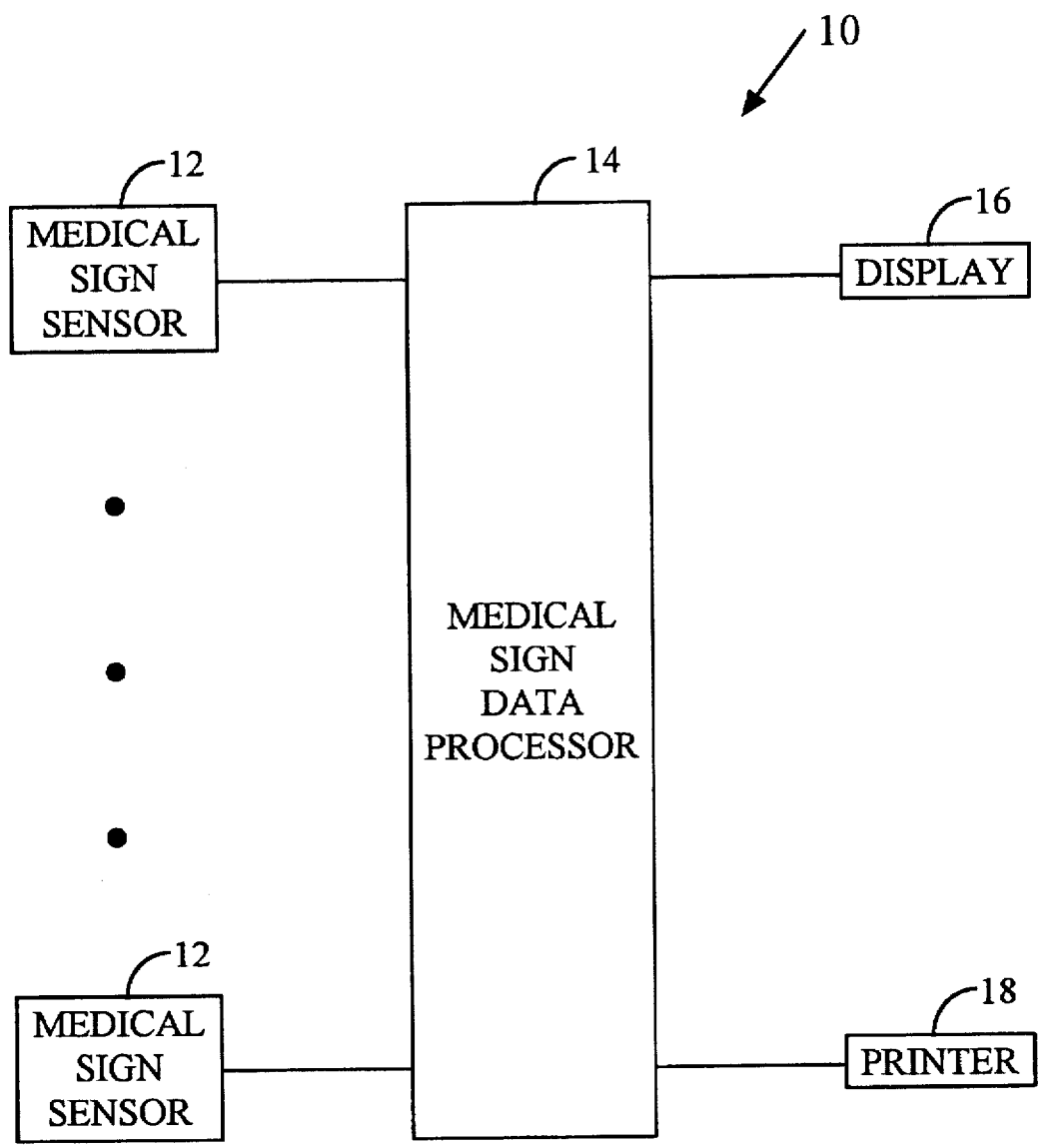
FIG. 1 is a block diagram of an automatic medical sign monitor.

In FIG. 1, automatic medical sign monitor 10 comprises medical sign sensors 12. Medical sign sensors 12 measure medical signs such as pulse rate, blood pressure, respiration, and body temperature and output data values representative of the medical signs as medical sign data to a medical sign data processor 14. Medical sign sensors 12 may be made according to techniques well known in the art. Medical sign data processor 14 collects a time ordered set of the medical sign data and finds the mean, up or down shifts in the mean, transients, variance, and changes in the variance for a selected time interval for each medical sign. The function of medical sign data processor 14 may be performed, for example, by a computer.

After finding the mean and variance of the medical sign data, medical sign data processor 14 applies a modified Fast Initial Response (FIR) Shewhart cumulative sum (CUSUM) algorithm to the mean and variance to detect a change in health state. If a change in health status is indicated, then medical sign data processor 14 displays the new health statistics on a display 16 and prints a log of the health status on a printer 18.

The modified FIR Shewhart cumulative sum algorithm assumes that the medical sign data is normally distributed around some normal value. Normal values for each medical sign may be determined from values collected from the general population.

A set of time ordered random variables $x_1 \ldots x_n$ of a medical sign normally distributed around two known states $F_1$ and $F_2$ defines a two-state Markov process, where the first state $F_1$ is associated with $x_1 \ldots x_m$ and the second state $F_2$ is associated with $x_{m+1} \ldots x_n$. To determine the point m where the medical sign changes from state $F_1$ to state $F_2$, let $$S_n = \sum_{k=1}^{n} \ln\left(\frac{f_2(x_k)}{f_1(x_k)}\right) - \min_{m \leq n} \sum_{k=1}^{m} \ln\left(\frac{f_2(x_k)}{f_1(x_k)}\right)$$

where m is chosen to maximize $S_n$. A change in Markov state from $F_1$ to $F_2$ occurs when $S_n > L$, where $S_n$ is the cumulative sum for the nth data point, and L is a constant chosen such that the reciprocal of the average run length equals the desired probability of false alarm. The probability of false alarm is approximately 0.005 for the two-state Markov process implemented.

$S_n$ may be calculated recursively according to:

$$S_n = \max\left(S(n-1) + \ln\left(\frac{f_2(x_n)}{f_1(x_n)}\right), 0\right)$$

In the FIR implementation of the Shewhart cumulative sum (CUSUM), $S_0 = L/2$.

Medical signs typically exhibit univariate distributions. For normal univariate distributions $F_1$ and $F_2$ having respective means $\mu_1$ and $\mu_2$ and standard deviation $\sigma$, then the upper cumulative sum for the nth data point may be found by the formula:

$$SH_n = \max\left(SH_{n-1} + \frac{x_n - \mu_1}{\sigma} - K, 0\right)$$

if $\mu_2 > \mu_1$, where $K = (\mu_2 - \mu_1)/2\sigma$. If $\mu_1 > \mu_2$, then the lower cumulative sum for the nth data point may be found by the formula:

$$SL_n = \max\left(SL_{n-1} + \frac{x_n - \mu_1}{\sigma} - K, 0\right)$$

where $K = (\mu_1 - \mu_2)/2\sigma$.

To estimate the number of data points t during the elapsed time from the time of change, i.e. from the time of the last zero mean value, a second set of SH and SL sums are calculated as above with $S_0 = 0$. The elapsed time is the time since the last zero value of $S_n$. The time of the change is the time of the last zero value of $S_n$. The shift in the mean caused by the change in the medical sign is then $$shift_n = \frac{\max(SL_n, SH_n + K)sign(SH_n - SL_n)}{t}$$

The current normal value of the medical sign may then be found by the equation predicted $x_n = \mu_1 + shift_n$. The Shewhart algorithm declares a change in state for any $x_k$ where $|x_k - \mu_1| \geq 3\sigma$. The FIR Shewhart CUSUM algorithm declares a change in state for $S_n > L$, or if $|x_k - \mu_1| \geq 3\sigma$ for $S_0 = L/2$.

The normal value for a medical sign may be determined from all of the available data or from a selected portion of the input data stream from a medical sensor 12. An initial baseline estimate from m data points of input data stream x is calculated as follows:

$$\text{baseline mean} = \frac{1}{m} \sum_{k=1}^{m} x_k$$

If a change is detected, such as an upward or downward shift or a transient, and the last m points indicate a change in the same direction, the mean and standard deviation may optionally be reset using all of the data history:

$$\text{mean} = \frac{1}{t} \sum_{k=n-t+1}^{n} x_k$$

where t=number of data points during the elapsed time. The standard deviation is estimated using the data collected since the last reset, including all of the data history but excluding the most recent data point and any outliers or burst points. If the standard deviation is zero, then the most recent data point is included in the calculation. A standardized value for the most recent data point is calculated as follows:

$$z_i = \sqrt{\frac{m}{m+i}} \left(\frac{x_i - \text{mean}}{\text{standard deviation}}\right)$$

where m=number of points used to estimate the mean and $z_i$ is set to zero if $x_i - \text{mean} = 0$.

The FIR Shewhart CUSUM algorithm is calculated using:

$SL_0 = L/2$ $SH_0 = L/2$ $SL_i = \max(0, SL_{i-1} - z_i - K)$ $SH_i = \max(0, SL_{i-1} + z_i - K)$ and the elapsed time and shift are calculated as above using:

$SL2_0 = 0$ $SH2_0 = 0$ $SL2_i = \max(0, SL2_{i-1} - z_i - K)$ $SH2_i = \max(0, SH2_{i-1} + z_i - K)$ A change in Markov state is declared if $SL_i$ or $SH_i$ is greater than or equal to L. A positive burst is declared if $z_i$ is greater than or equal to 3 and a negative burst is declared if $z_i$ is less than or equal to $-3$. An outlier is declared if $2 \leq |z_i| < 3$. If automatic reset is selected and a shift or burst is declared, then $SH_i$ and $SL_i$ are reset to L/2 and $SH2_i$ and $SL2_i$ are reset to zero. In the current implementation, the default value of L is 4.

For monitoring the variance of distributions $F_1$ and $F_2$, let $\sigma_2^2 = C\sigma_1^2$ if $\sigma_2^2 \geq \sigma_1^2$, and $\sigma_1^2 = C\sigma_2^2$ if $\sigma_1^2 \geq \sigma_2^2$. Then:

$$SH_n = \max\left(SH_{n-1} + \frac{(x_n - \mu)^2}{\sigma_1^2} - K_1, 0\right)$$

and $$SL_n = \max\left(SL_{n-1} + \frac{(x_n - \mu)^2}{\sigma_1^2} - K_2, 0\right)$$

where $$K_1 = (\ln C)\left(\frac{C}{C-1}\right)$$

and $$K_2 = (\ln C)\left(\frac{1}{C-1}\right)$$

Note that if $\mu$ and $\sigma$ are unknown, then $$\frac{(x_n - \mu)^2}{\sigma_1^2}$$

has a Hotelling $T^2$ statistical distribution. The estimated shift in variance is then $$shift_n = -\frac{SL_n}{\text{number of data points during elapsed time}} + 0.811$$

if $SL_n$ is greater, and $$shift_n = \frac{SH_n}{\text{number of data points during elapsed time}} + 1.216$$

if $SH_n$ is greater, where the elapsed time is the time since the last $SL_n$ or $SH_n$ zero value. The current variance estimate is given by the shift times $\sigma_1^2$.

The variance ratio is calculated from the mean. As defined above, the mean is given by the formula:

$$\text{mean} = \frac{1}{t} \sum_{k=n-t+1}^{n} x_k$$

where t=the number of data points during the last $SL_n$ or $SH_n$ zero value. The variance ratio is given by the formula:

$$\frac{(x_k - \text{mean})^2}{\sigma_1^2}$$

The variance cumulative sum is calculated using
$SL_0=0$
$SH_0=0$
$SL_k=\max(0, SL_{k-1})+\text{variance ratio}+0.811)$
$SH_k=\max(0, SH_{k-1})+\text{variance ratio}-1.216)$ A change in Markov state is declared if $SL_k$ is greater than a lower threshold of, for example, 9 or if $SH_k$ is greater than an upper threshold of, for example, 13. The variance has decreased if $SL_i$ crossed the lower threshold, and has increased if $SH_k$ crossed the upper threshold. The thresholds are set such that the reciprocal of the average run length equals the desired probability of false alarm. Default settings of 9 and 13, respectively result in a probability of false alarm of approximately 0.005 with 0.0025 in each of the tails of the distribution.

A future value of a monitored sign may be forecast by a weighted rate of change. The time history of the values of a medical sign may be represented by a set of time ordered pairs $((x_1,t_1),(x_2,t_2) \ldots ,(x_n,t_n))$ having a value $x_k$ at a time $t_k$. The rate of change at time $t_k$ may then be estimated by:

$$R_k = \left( \frac{x_k - x_{k-1}}{t_k - t_{k-1}} \right)$$

A weighted rate of change based on, for example, six points, may then be calculated using a two point estimate as follows:

$$WR_k = \frac{5R_k + 4R_{k-1} + 3R_{k-2} + 2R_{k-3} + R_{k-4}}{15}$$

The predicted value for time k+1 is then $PX_{k+1}=x_k+WR_k (t_{k+1}-t_k)$. Alternatively, a damped predictor may be used as follows:

$$DP_{k+1}=x_k+WR_k ln(t_{k+1}-t_k)$$

The variance of the weighted rate is given by:

$$VAR_k = \left( \frac{1}{14} \right) (5(R_k - WR_k)^2 + 4(R_{k-1} - WR_{k-1})^2 +$$
$$3(R_{k-2} - WR_{k-2})^2 + 2(R_{k-3} - WR_{k-3})^2 + (R_{k-4} - WR_{k-4})^2)$$

and the standard deviation of the weighted rate is given by:

$$WS_k = \sqrt{VAR_k}$$

A two sigma confidence interval for the damped predicted value at time $t_{k+1}$ may then be found by the formula:

$$DP_{k+1} \pm 2WS_k ln(t_{k+1}-t_k)$$

A quadratic regression may also be performed to forecast a predicted value of an observed medical sign by solving $$X=\alpha+\beta T+\gamma T^2$$

for coefficients $\alpha$, $\beta$, and $\gamma$, where X is the matrix of the values of the observed medical signs and T is the matrix of the times of the observations. Substituting estimated values for coefficients $\alpha$, $\beta$, and $\gamma$ derived from the application of a quadratic regression then gives the predicted values of the medical signs.

The following prediction equations for estimating Hansen's disease Erythema Nodosum Leprosum (ENL) and reversal reaction severity were developed from nonlinear multivariate regression techniques:

$$\text{estimated ENL reaction} = 3.843 + 1.264 \left( \frac{\Delta S}{\Delta T} \right) + 0.167 \left( \frac{\Delta S}{\Delta T} \right)^2 -$$
$$0.325 \left( \frac{\Delta S}{\Delta T} \right)(BI) + .0824 (BI)^2 - 0.129 (BI)^3 + .033 \left( \frac{\Delta S}{\Delta T} \right)^3 +$$
$$0.697(BI)\left( \frac{\Delta TEMP}{\Delta T} \right) + 0.342(BI)\left( \frac{\Delta D}{\Delta T} \right) + .018(BI)\left( \frac{\Delta W}{\Delta T} \right) -$$
$$.063(D) - .022(TEMP) + 19.886 \left( \frac{\Delta TEMP}{\Delta T} \right)^2 - 1.121 \left( \frac{\Delta D}{\Delta T} \right)^2$$

and
estimated reversal reaction = $-74.973 - .023(S) + .794(TEMP) + .024(BI)(S) + .004(D) - 1.132(BI)^2$ where:
S=systolic blood pressure
D=diasystolic blood pressure
BI=bacilli index
TEMP=temperature
W=weight
T=time The bacilli index may be forecast using the following two prediction equations developed from multivariate regression techniques:

estimated bacilli index = $-46.834 + 16.148$ (reversal reaction) + (TEMP) $- .162$(reversal reaction) (TEMP)
and
estimated bacilli index = $46.172 + .0025(\Delta S)^2 + .052$(ENL reaction)$^2 - .00468$(TEMP)$^2$ Medication compliance may be monitored by comparing the amounts prescribed with the amounts consumed over time.

Figure 2:
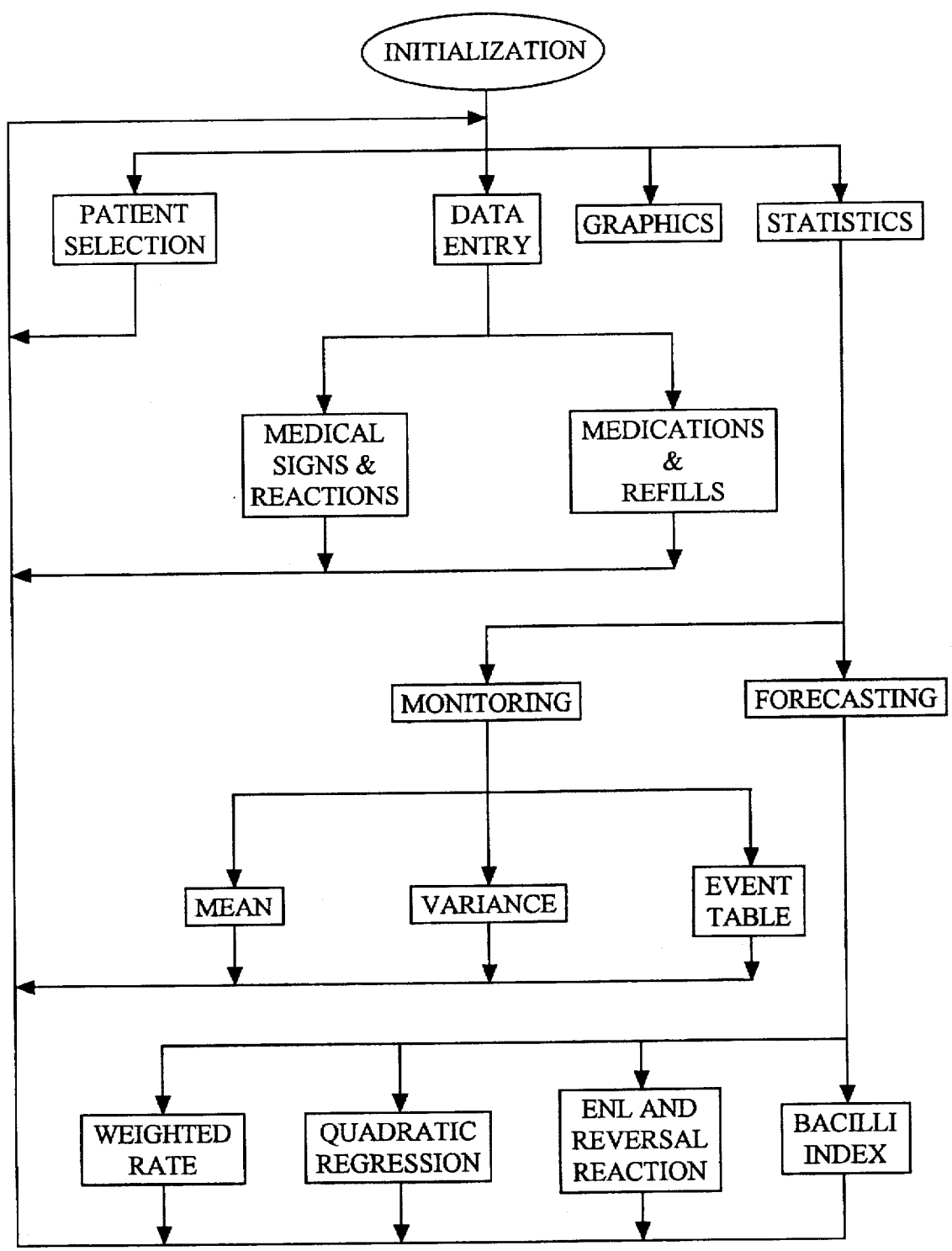
FIG. 2 is a flow chart of initialization of the medical sign data processor.

In one embodiment of the automatic medical sign monitor, an initialization of the medical sign data processor is performed by the user to select setup, data entry, statistics, and graphics. FIG. 2 is a flow chart illustrating the initialization of the medical sign data processor. The patient selection function allows the user to select the location of patient medical data files used by the medical sign data processor.

The data entry function allows the user to select the medical sign data to be input and the prescribed medications to be monitored for compliance.

The statistics function allows the user to select monitoring and forecasting functions to be applied to the medical sign data. Monitoring functions include mean monitoring, variance monitoring, and event table monitoring. The mean monitoring function flags shifts, bursts, and outliers in the selected interval of medical sign data. The variance monitoring function flags changes in variance. The event table function combines statistically significant events in the mean and variance for all the selected medical signs in a tabular format.

The forecasting function allows the user to select medical sign forecasting based on weighted rate, quadratic regression, ENL and reversal reaction, and bacilli index. Weighted rate or quadratic regression based forecasting may be performed on any medical sign data selected by the user. The ENL and reversal reaction forecasting and bacilli index forecasting are specific to Hansen's disease patients.

The graphics function provides a visual representation of the statistical and forecasting function results.

Figure 3:
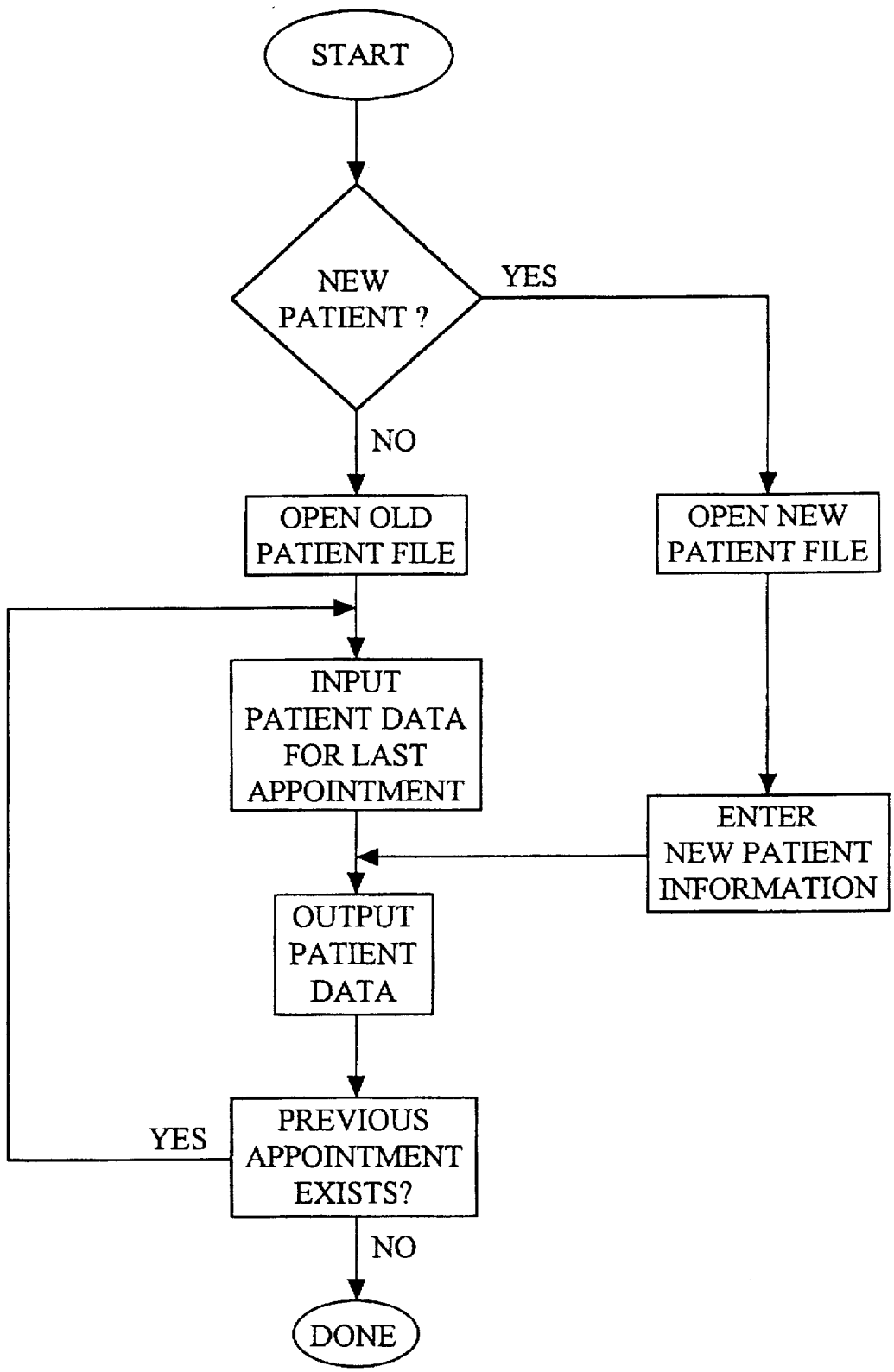
FIG. 3 is a flow chart of the patient selection function.

FIG. 3 is a flow chart of the patient selection function. If a new patient is to be entered, then a new patient file is opened and the time since initial visit is reset. Otherwise, the patient file is opened and the last appointment information is input. The number of days since the initial appointment is determined and is output along with the current medical sign statistics. If there was a previous appointment, then the previous appointment data is input and the number of days since the initial appointment is output along with the previous medical sign statistics. Each further previous appointment is similarly processed and displayed.

Figure 4:
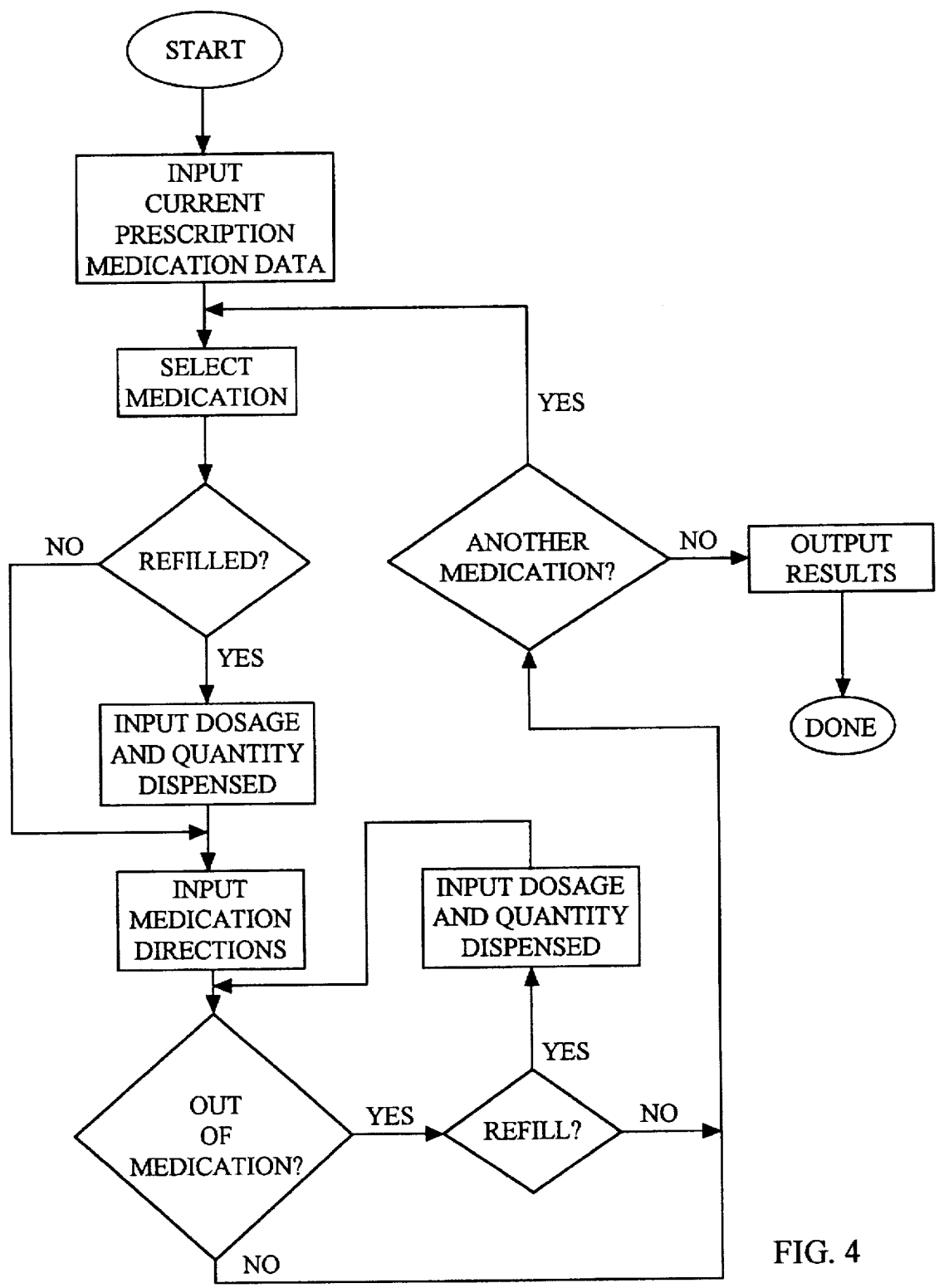
FIG. 4 is a flow chart of the medication monitoring function.

FIG. 4 is a flow chart of the medication monitoring function. Medication information is input including the prescription date and the quantity dispensed. Refill quantities are compared with prescription directions to estimate consumption. As prescriptions are entered, medication shortfalls are displayed.

Other modifications, variations, and applications of the present invention may be made in accordance with the above teachings other than as specifically described to practice the invention within the scope of the following claims.

I claim:

1. An automatic medical sign monitor comprising:
a medical sign sensor for collecting a time ordered set of medical sign data;
a medical sign data processor coupled to said medical sign sensor for detecting a change in health state by forming statistics from said medical sign data comprising:
a fast initial response (FIR) Shewhart cumulative sum modified to include:
a Shewhart statistic having a first upper threshold and a first lower threshold selected to result in a probability of false alarm substantially equal to a reciprocal of an average run length,
a fast initial response cumulative sum having a second upper threshold and a second lower threshold selected to result in a probability of false alarm substantially equal to said reciprocal of said average run length for detecting a shift in mean value,
and a second cumulative sum for estimating a current mean value and an elapsed time of said shift in mean value;
and a variance cumulative sum modified to detect a shift in variance and to estimate a current variance value and an elapsed time of said shift in variance, and to include a third upper threshold and a third lower threshold selected to result in a probability of false alarm substantially equal to said reciprocal of said average run length;
and an output device coupled to said data processor for outputting at least one of said medical sign data and said statistics.

2. The automatic medical sign monitor of claim 1 wherein said output device comprises a display.

3. The automatic medical sign monitor of claim 1 wherein said output device comprises a printer for logging said statistics.

4. The automatic medical sign monitor of claim 1, wherein said statistics further include an event table of said medical sign data.

5. The automatic medical sign monitor of claim 1 wherein said statistics further include at least one of weighted rate of change, damped weighted rate of change, quadratic regression, and prediction equations developed from non-linear multivariate regression techniques for forecasting future values of said medical signs.

6. The automatic medical sign monitor of claim 1 wherein said medical sign data processor compares dispensed quantities of medication with prescription directions to estimate consumption and displays medication shortfalls.

7. The automatic medical sign monitor of claim 1 wherein said medical sign processor forecasts estimates of Hansen's disease Erythema Nodosum Leprosum (ENL) reaction, reversal reaction, and bacilli index from prediction equations developed from non-linear multivariate regression techniques.

8. A method for automatically monitoring medical signs comprising the steps of:
sensing medical signs to form a time ordered set of medical sign data;
detecting a change in health state by forming statistics from the medical sign data comprising:
a fast initial response (FIR) Shewhart cumulative sum modified to include:
a Shewhart statistic having a first upper threshold and a first lower threshold selected to result in a probability of false alarm substantially equal to a reciprocal of an average rim length,
a fast initial response cumulative sum having a second upper threshold and a second lower threshold selected to result in a probability of false alarm substantially equal to the reciprocal of the average run length for detecting a shift in mean value,
and a second cumulative sum for estimating a current mean value and an elapsed time of said shift in mean value;
and a variance cumulative sum modified to detect a shift in variance and to estimate a current variance value and an elapsed time of the shift in variance, and to include a third upper threshold and a third lower threshold selected to result in a probability of false alarm substantially equal to the reciprocal of the average run length;
and outputting at least one of the medical sign data and the statistics.

9. The method of claim 8 wherein the step of outputting forecasts includes displaying the medical sign data and statistics.

10. The method of claim 8 wherein the step of outputting forecasts includes logging the statistics on a printer.

11. The method of claim 8 wherein the step of outputting forecasts includes forming an event table of the medical sign data.

12. The method of claim 8 wherein the step of forming statistics further includes at least one of weighted rate of change, damped weighted rate of change, quadratic regression, and prediction equations developed from non-linear multivariate regression techniques for forecasting future values of the medical signs.

13. The method of claim 8 further including the step of comparing dispensed quantities of medication and prescription directions to estimate consumption and displaying medication shortfalls.

14. The method of claim 8 further including the step of estimating Hansen's disease Erythema Nodosum Leprosum (ENL) reaction, reversal reaction, and bacilli index forecasts from prediction equations developed from non-linear multivariate regression techniques.

* * * * *